(12) United States Patent
Hollingsworth et al.

(10) Patent No.: US 7,342,010 B2
(45) Date of Patent: Mar. 11, 2008

(54) 2-THIAQUINOLIZIDINES AND PROCESS FOR THE PREPARATION THEREOF

(75) Inventors: Rawle I. Hollingsworth, Haslett, MI (US); Li Gao, Williamston, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 549 days.

(21) Appl. No.: 10/988,688

(22) Filed: Nov. 15, 2004

(65) Prior Publication Data

US 2006/0106212 A1 May 18, 2006

(51) Int. Cl.
*A61K 31/542* (2006.01)
*C07D 513/04* (2006.01)
(52) U.S. Cl. ...................... 514/224.2; 544/47
(58) Field of Classification Search ................ 546/114; 514/301, 224.2; 544/47
See application file for complete search history.

(56) References Cited

U.S. PATENT DOCUMENTS 5,643,888 A 7/1997 Rohrschneider

FOREIGN PATENT DOCUMENTS

EP 0034015 A 8/1981

OTHER PUBLICATIONS

Winterfeld, K., et al., 1-(2-Chloroethyl)-2-chloromethylpiperidineChemische Berichte92 1510-17 (1959).
Hadley, Michael Stewart, et al., Pharmaceutically active compounds. Eur. Pat. Appl. (1981), 71 pp. Coden: EPXXDWEP 34015 A2 19810819 CAN 96:6743 AN 1982:6743 CAPLUS.
Legler, G., Adv. Carbohydr. Chem. Biochem. 48 319-384 (1990).
Truscheit, E., et al., Angew. Chem. Int. Ed. Engl. 20 744 (1981).
Anzeveno,P.B., et al., J. Org. Chem. 54 2539 (1989).
Platt, F.M., et al., Science 276 428 (1997).
Karpas, A., et al., Proc. Natl. Acad. Sci. U.S.A. 85 9229 (1988).
Fleet, G.W.J., et al., FEBS Lett. 237, 128 (1988).
Gross, P.E., et al., Clin. Cancer Res. 1, 935 (1995).
Kino, I., et al., J. Antibiot. 38, 936 (1985).
Elbein, A.D. FASEB J. 5, 3055 (1991).
Robinson, K.M., et al., Diabetes 40, 825 (1991).
EPO-Communicationand Search Report, European Patent Application No. 05024562.0.
Rink et al., "Syntheses des 2-thiachinolizidins", NATURWISSENSCHAFTEN, vol. 44, 1957, pp. 559.
Winterfeld et al., "Zur Kenntnis des 1-beta-Chlor-athyll-2-chlormethyl-piperidns", Chem. Ber., vol. 92, 1959, pp. 1510-1517.
Asano N et al., "Sugar-mimic glycosidase inhibitors: natural occurrence, biological activity and prospects for therapeutic application", Tetrahedron: Asymmetry, Elsevier Science Publishers, Amsterdam, NL, vol. 11, No. 8, May 2000, pp. 1645-1680.

*Primary Examiner*—Bernard Dentz
(74) *Attorney, Agent, or Firm*—Ian C. McLeod

(57) ABSTRACT

A process for producing 2-thiaquiolizidines which are glycosidase and glycosyltransferase inhibitors is described. The compounds are of the formula:

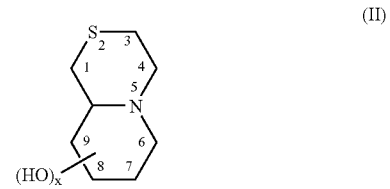

where x is 0 to 3.

15 Claims, 8 Drawing Sheets

D-gluco

L-ido

D-manno

D-galacto

L-altro

L-gulo

D-gluco

L-ido

D-manno

D-galacto

L-altro

L-gulo

R = Hydrogen or a protecting group

2-THIAQUINOLIZIDINES AND PROCESS FOR THE PREPARATION THEREOF

CROSS-REFERENCE TO RELATED APPLICATION

None

STATEMENT REGARDING FEDERALLY SPONSORED RESEARCH OR DEVELOPMENT

None

BACKGROUND OF THE INVENTION (1) Field of the Invention

The present invention relates to a process for the preparation of 2-thiaquinolizidines which are selective α-glycosidase inhibitors having the formula:

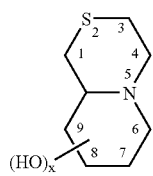

where x is 0 to 3. In particular, the present invention relates to thiaquinolizidines which are derived from a mono-, or di-glycoside with protected hydroxyl groups, if present, by a synthetic route which reacts a 6-halo-5-ulosonic acid ester with a 2-aminoalkanethiol to form a 6-membered thiazine ring in which the nitrogen is in the form of a hemiaminal or imine and then reduction of the hemiaminal or imine to form an intermediate amino acid ester which cyclizes to form a lactam. Reduction of the lactam and deprotection of any protected hydroxyl groups forms the 2-thiaquinolizidine.

(2) Description of Related Art

Mono- and dihydroxy substituted 2-thiaquinolizidines are known. They are described in Winterfeld, K., et al., 1-(2-Chloroethyl)-2-chloromethylpiperidine. Chemische Berichte 92 1510-17 (1959); Rink, M., et al., Synthesis of 2-thiaquinolizidine and its S,S-dioxide. Arch. Pharm. 292 165-9 (1959); Gorlach, G. A., et al., New Synthesis of plezhicil. Meditsinskaya Promyshlennost SSSR 13 (No. 4), 35-40 (1959); Rink, Melanie, et al., Synthesis of 2-thiaquinolizidine. Naturwissenschaften 44 559 (1957); and Hadley, Michael Stewart, et al., Pharmaceutically active compounds. Eur. Pat. Appl. (1981), 71 pp. CODEN: EPXXDW EP 34015 A2 19810819 CAN 96:6743 AN 1982:6743 CAPLUS. They are used as intermediates to other compounds.

Compounds incorporating 5-aza-1-deoxyglycosides or a 1,5-imino-1,5-dideoxyalditol substructure are known in the art. They are generally aza-sugars or iminoalditols. Examples are castanospermine 1 and deoxynojirimycin 2. These compounds are often potent glycosidase or glycosyltransferase inhibitors.

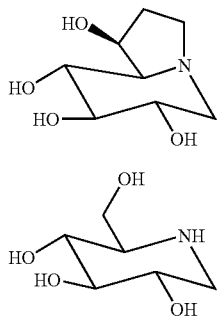

Despite their promise, glycosidase inhibitors such as castanospermine 1, and deoxynojirimycin 2, have not realized their full clinical potential. This is largely because of a lack of commercially viable syntheses and difficulty in preparing a comprehensive palette of variant structures. In some cases such as deoxynojirimycin there is also the problem of too low specificity for a particular enzyme (Legler, G., Adv. Carbohydr. Chem. Biochem. 48 319-384 (1990); and Vandenbroek, L. A. G. M., et al., Rec. Trav. Chim. Pays Bas 112 82 (1993)). Iminoalditols are typically plant alkaloids and many of the possible drug candidates are available in only small exploratory amounts. The potential medical applications for these compounds and their derivatives are numerous and range from diabetes (Truscheit, E., et al., Angew. Chem. Int. Ed. Engl. 20 744 (1981); Anzeveno, P. B., et al., J. Org. Chem. 54 2539 (1989); Witczak, Z. J., Carbohydrates as New and Old Targets for Future Drug Design. In Carbohydrates in Drug Design; Witczak, Z. J., Ed.; Marcel Dekker Inc.; New York Page 1 (1997); and Platt, F. M., et al., Science 276 428 (1997)) and other metabolic disorders through antimicrobials (Karpas, A., et al., Proc. Natl. Acad. Sci. U.S.A. 85 9229 (1988); Fleet, G. W. J., et al., FEBS Lett. 237, 128 (1988); Taylor, D. L., et al., AIDS 5, 693 (1991); Hirsh, M. S., U.S. Pat. No. 5,011,826 (1991); and Rohrschneider, L. R., U.S. Pat. No. 5,643,888 (1997)), cancer (Gross, P. E., et al., Clin. Cancer Res. 1, 935 (1995)), autoimmune diseases (Kino, I., et al., J. Antibiot. 38, 936 (1985); Cenci di Bello, I., et al., Biochem. J. 259, 855 (1989); Elbein, A. D. FASEB J. 5, 3055 (1991); Goss, P. E., et al., Clin. Cancer Res. 1, 935 (1995); Das, P. C., et al., Oncol. Res. 7, 425 (1995); and Elbein, A. D., et al., In Iminosugars as Glycosidase Inhibitors; Stutz, A. E., Ed.; Wiley-VCH: Weinheim, pp 216-251 and references therein (1999)), neurological (Molyneux, R. J., et al., J. Nat. Prod. 58, 878 (1995)) and metabolic (Robinson, K. M., et al., Diabetes 40, 825 (1991); and Balfour, J. A., et al., Drugs 46 1025 (1993)) disorders. Because of their rigidity and the added interaction of the second ring, bicyclic systems such as in compound 1 are especially interesting.

Objects

It is therefore an object of the present invention to provide novel bicyclic systems containing 1,5-dideoxy-1,5-imino functionality which should have wide biochemical uses especially as glycosidase and glycosyltransferase inhibitors. It is further an object of the present invention to provide a novel process for the preparation of such compounds. These and other objects will become increasingly apparent by reference to the following description.

SUMMARY OF THE INVENTION

The present invention relates to a process for the preparation of a compound (I) of the formula:

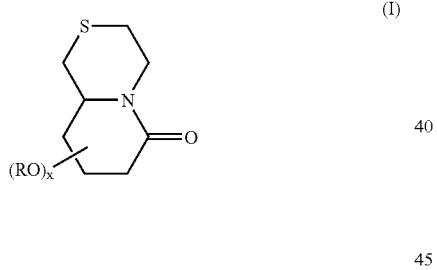
(I)

which comprises reacting a hydroxyl protected 6-bromo-5-ulosonic acid alkyl ester first with a 2-aminoalkanethiol and then with a reducing agent to produce the compound (I), wherein R is a protecting group for the reaction and x is 0 to 3.

The present invention also relates to the process wherein in addition the compound of the formula:

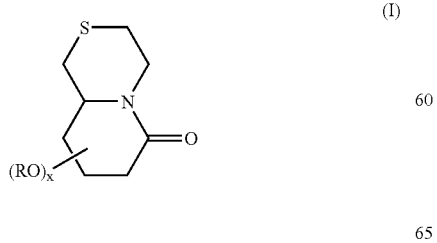
(I)

is reduced and deprotected to produce a compound (II) of the formula:

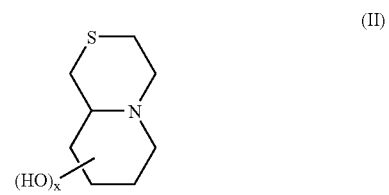
(II)

In particular the present invention relates to a process for the preparation of a compound (III) of the formula:

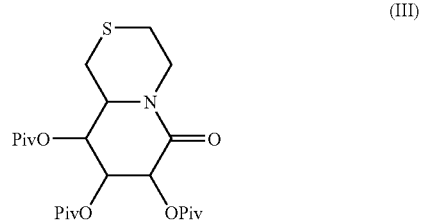
(III)

which comprises reacting 1-methyl-6-bromo-2,3,4-pivaloyl (Piv)-5-ulosonic acid ester with mercaptoethylamine and a reducing agent to produce the compound (III). The present invention also relates to a process wherein in addition the compound (III) is reduced and deprotected to produce a compound (IV) of the formula

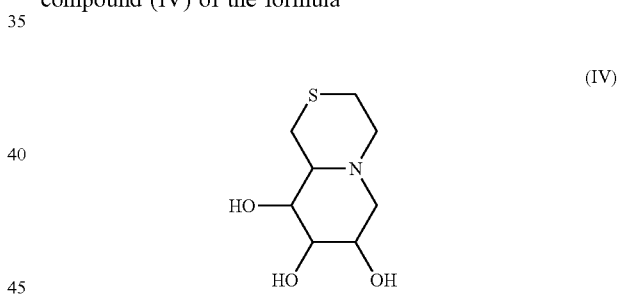
(IV)

Preferably the process produces the lactam compound (III):

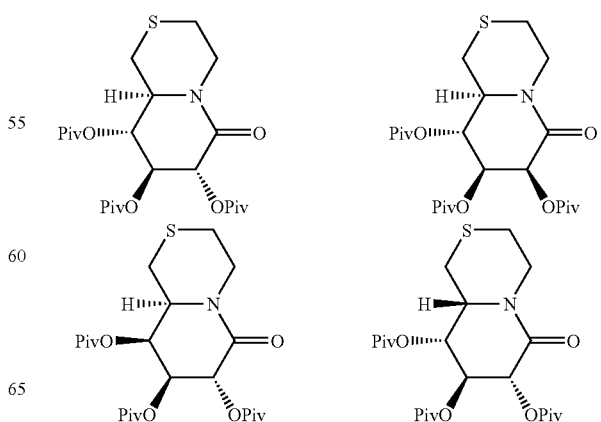

-continued

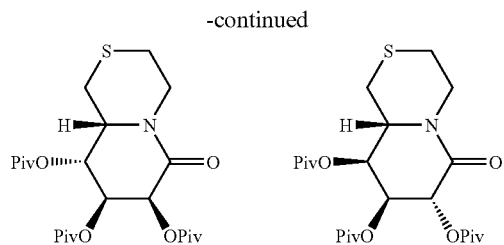

Preferably the process produces derivative compound (IV):

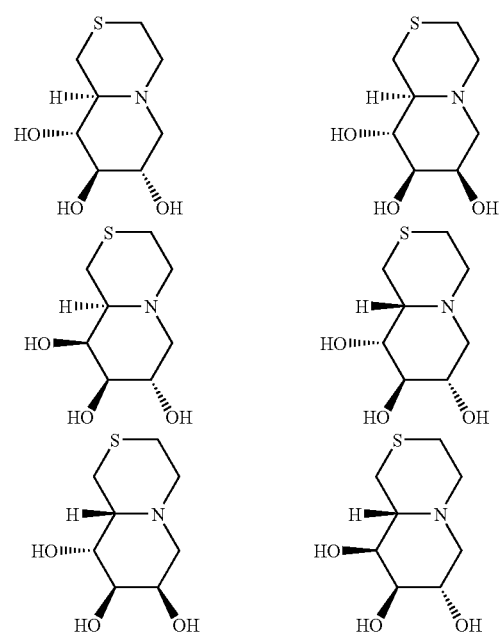

The present invention relates to a compound (II) of the formula

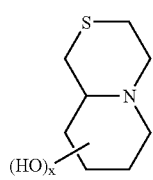

where x is 0 to 3.
Preferably the compound of the formula IV is:

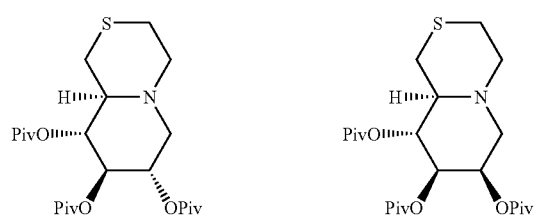

-continued

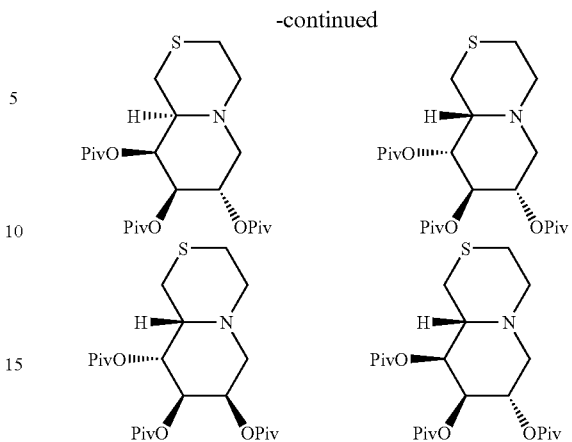

The present invention relates to a compound (I) of the formula:

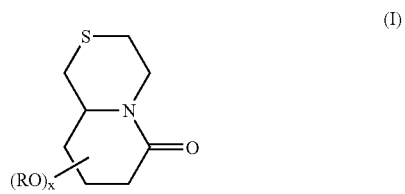

where x is 0 to 3, and R is a protecting group.

The present invention also relates to a method for inhibiting an enzyme which comprises reacting the enzyme with a suitable substrate in the presence of a compound (II) of the formula:

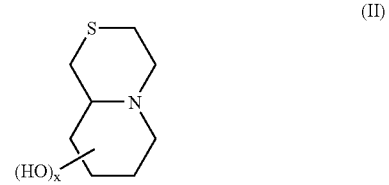

where x is 0 to 3.

In the method the enzyme can be inhibited in vitro. In the method the enzyme can be inhibited in vivo in an animal.

The present invention relates to a process for the preparation of a compound (II) of the formula:

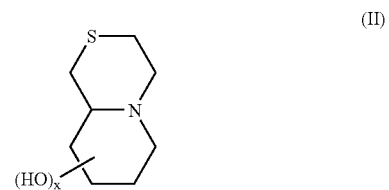

which comprises reacting a compound (I) of the formula

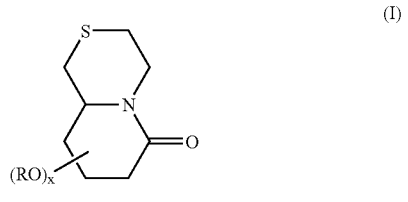

(I)

where R is a protecting group and x is 2 or 3 with a reducing agent and then a deprotecting agent to produce the compound (II). In the process the compound (IV) prepared preferably has the formula:

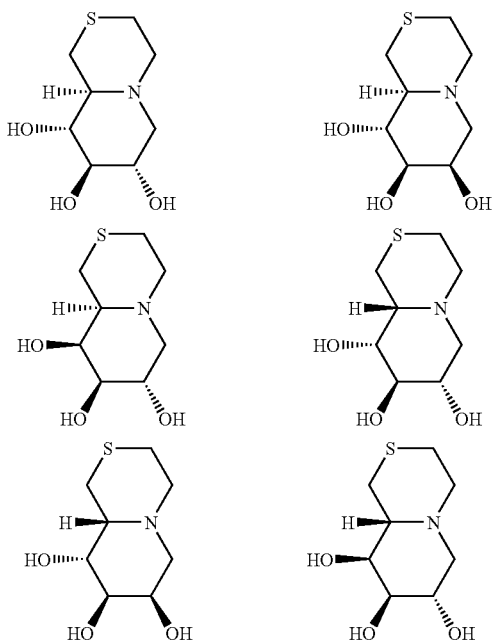

where x is 3. Preferably in the process, R is pivaloyl and the reducing agent is borane and the deprotecting agent is sodium methoxide.

Description of Preferred Embodiments

The present invention relates to the preparation of the compounds of the formula:

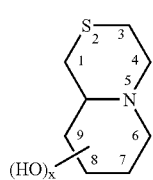

(II)

Figure 1:
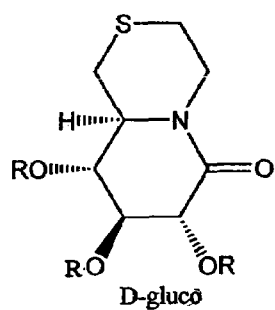
FIG. 1 shows a series of lactams and their 2-thiaquinolizidine reduction products that can be prepared by the process of the present invention. These include the D-gluco, L-ido, D-manno and L-gulo compounds.
Figure 1:
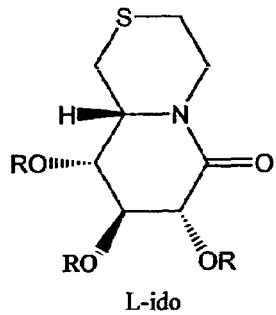
Figure 1:
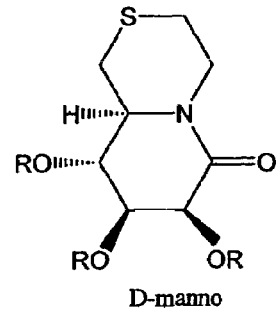
Figure 1:
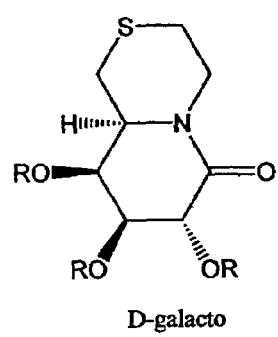
Figure 1:
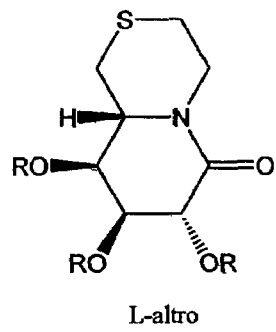
Figure 1:
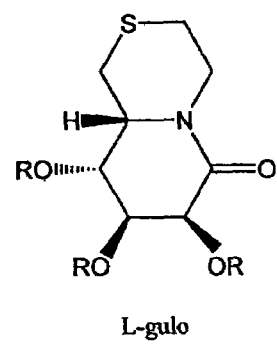
Figure 1:
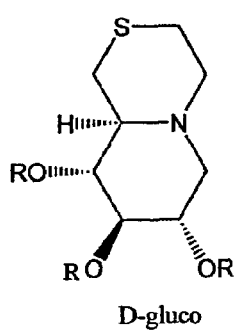
Figure 1:
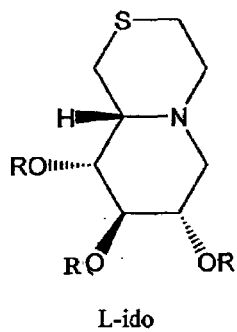
Figure 1:
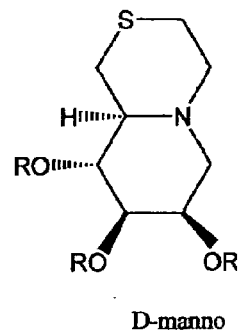
Figure 1:
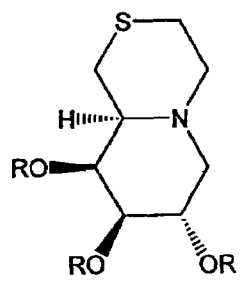
Figure 1:
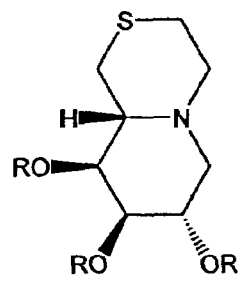
Figure 1:
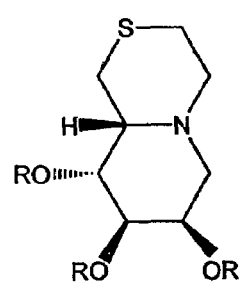

The preferred compounds are shown in FIG. 1. The present invention relates to synthesis of a preferred 2-thiaquinolizidine which has the formula 3

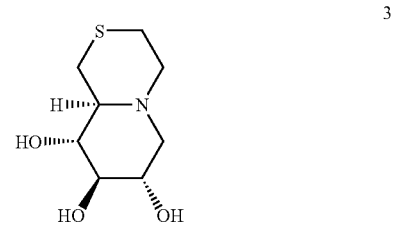

3 and related compounds in which an O-6 of analogous hexose compounds was replaced by a sulfur atom. The 6-position to the ring nitrogen is bridged with a 2-carbon and sulfur fragment to form a 2-thiaquinolizidine ring system thus increasing rigidity and increasing lipophilicity. Such a system has never been reported and circumvents in the formation of a carbon-carbon bond involving the 6-position. The presence of sulfur at a position that is normally oxygenated is also a decided advantage since compounds with differing configurations at the various carbon centers and differing substitution patterns can be made for obtaining compounds with useful therapeutic potential.

7(S),8(R),9(R)-Trihydroxy-2-thiaquinolizidine 3 is a new bicyclic dideoxy-iminohexitol glycosidase inhibitor derivative with nominally the D-gluco-configuration. X-ray analyses indicated that the preferred conformation was a flat trans-fused system. Unlike deoxynojirimycin, this inhibitor was selective for α-glucosidases (yeast and rice) and showed no inhibitory activity towards β-glucosidases (almond), α-galactosidase (green coffee beans), α-galactosidases (E-coli) and α-mannosidases (jack bean).

Scheme 1 shows the reaction scheme for the D-gluco compound which is the same for all of the compounds.

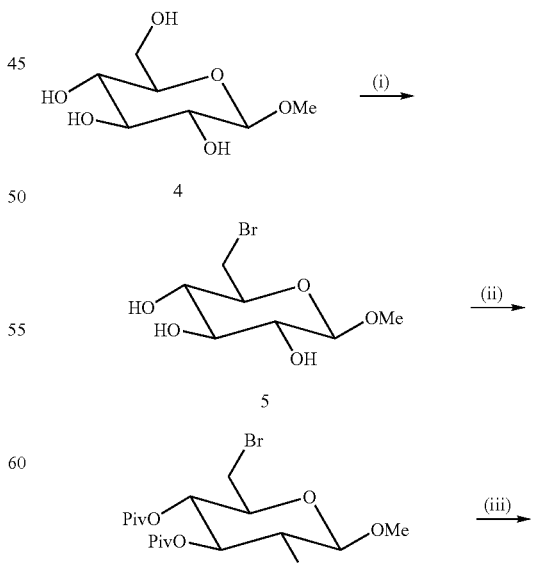

Scheme 1

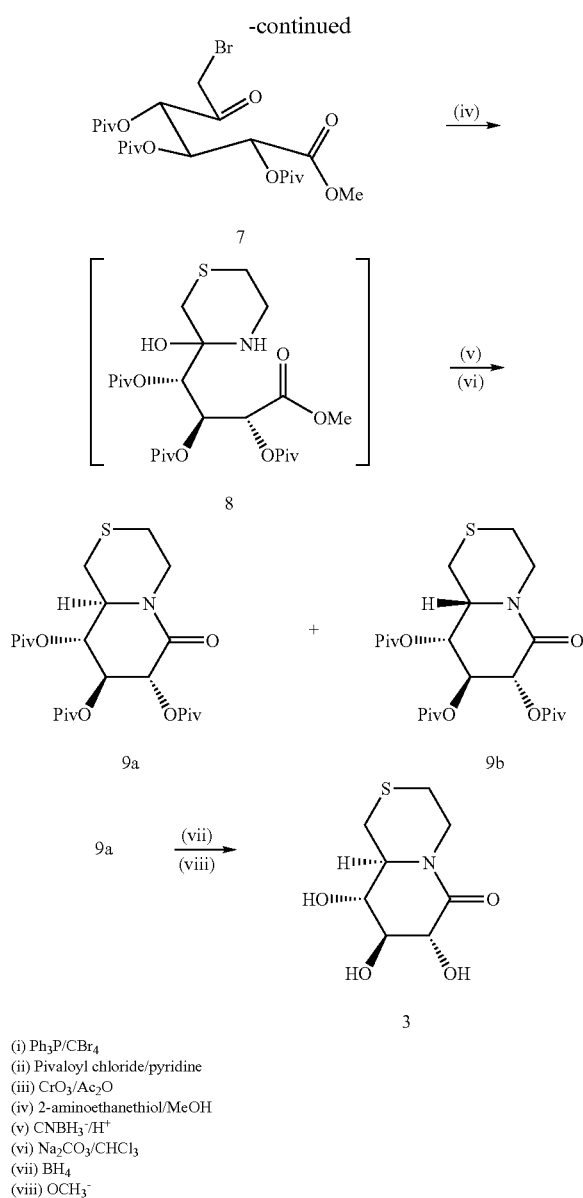

(i) Ph₃P/CBr₄
(ii) Pivaloyl chloride/pyridine
(iii) CrO₃/Ac₂O
(iv) 2-aminoethanethiol/MeOH
(v) CNBH₃⁻/H⁺
(vi) Na₂CO₃/CHCl₃
(vii) BH₄
(viii) OCH₃⁻

A key feature of the reaction scheme is the oxidation of a 6-bromo β-glycoside to give a 6-bromo-5-ulosonic acid alkyl ester. Reaction of this α-halo ketone with a 2-aminoalkanethiol leads to rapid thioether formation and immediate cyclization to an aminal which quickly forms an imine. Reduction of the aminal or imine by hydride (e.g borane or cyanoborohydride) yields an amine which can then be cyclized to form a lactam. Reduction of the lactam yields the thiaquinolizidine system.

Thus the reaction sequence involved the preparation of a peracylated 6-bromo-6-deoxy-glycoside 6 which was oxidized to a 5-ulosonic acid ester 7 with chromium trioxide. Treatment of 7 with 2-aminoethanethiol yielded the aminal 8 directly. This was reduced and cyclized to the desired lactam 9a and the L-ido isomer 9b. Reduction of the lactam 9a with borane and deacylation yielded compound 3. Some L-ido product (9b) was formed at the reductive amination stage. This was readily seperated by silica chromatography. There was some variability in the actual amount formed ranging from traces to 2.5:1 in favor of the D-gluco analog. The final and intermediate products were characterized by a very high degree of crystallinity.

Experimental

General Procedures:

Melting points were measured on a Ficher-Johns melting point apparatus. Optical rotations were measured ($\lambda$=589 nm) at room temperature using a Jasco P-1010 polarimeter. IR spectra were recorded on a FT-IR instrument. The $^1$H (and $^{13}$C) NMR spectra were recorded at 500 (125.5) MHz on a Varian VXR spectrometer. The HRMS FAB mass spectra were obtained using a Jeol HX-110 double-focusing mass spectrometer operating in positive ion mode.

Synthetic Methods:

Methyl 6-Bromo-6-deoxy-β-D-glucopyranoside (5) To a stirred solution of methyl β-D-glucopyranoside 4 (10.15 g, 50 mmol) in anhydrous pyridine (300 mL) at 0° C. were added triphenylphosphine (26.2 g, 100 mmol) and carbon tetrabromide (24.87 g, 75 mmol). The resulting mixture was protected from moisture and stirred at 0° C. for ten minutes, then was allowed to warm to 65° C. and was stirred for 4 hours. Methanol (10 mL) was added to decompose any excess of reagent. The solvent was removed by evaporation and the residue was purified by column chromatography ($CH_2Cl_2$, followed by 20:1 $CH_2Cl_2$/MeOH). Crystallization from methanol-hexanes afforded white crystalline solid (10.96 g, 85%), m.p. 139-140° C., $[\alpha]^{20}_D$=−27.6° (c 0.22, $H_2O$).

Methyl 6-Bromo-6-deoxy-2,3,4-tri-O-pivaloyl-β-D-glucopyranoside (6) Pivaloylation of 5 (6.73 g, 26 mmol) by trimethylacetyl chloride (28.8 mL, 32.4 mmol) in pyridine (300 mL) at room temperature for 2 days afforded an white solid 6 (11.2 g, 84%), m.p. 109-110° C., $[\alpha]^{20}_D$=−2.4° (c 0.31, $CHCl_3$). IR ($CH_3Cl$) $v_{max}$ 2971.7, 1745.6, 1140.9 cm$^{-1}$. $^1$H NMR (500 MHz, $CDCl_3$) δ 5.29 (1H, t, J=9.5 Hz), 4.99 (2H, t, J=9.7 Hz), 4.42 (1H, d, J=8.0 Hz), 3.70 (1H, m), 3.50 (3H, s), 3.39-3.12 (2H, m), 1.14 (9H, s), 1.13 (9H, s), 1.08 (9H, s); $^{13}$C NMR (125.5 MHz, $CDCl_3$) δ 177.14, 176.63, 176.51, 101.36, 73.7, 71.9, 71.2, 70.8, 57.1, 38.8, 38.7, 30.6 ppm; HR-FABMS (M+H⁺) Calcd. 509.1750, found 509.1736.

Methyl 6-Bromo-2,3,4-tri-O-pivaloyl-5-keto-easter (7) To a solution of 6 (1 g, 1.96 mmol) in acetic acid (100 mL) and acetic anhydride (10 mL), chromium trioxide (1.18 g, 11.8 mmol) was added and the suspension was stirred at room temperature for 3 hours. The mixture was then poured slowly into cold water (500 mL). The water was extracted 5 times with $CH_2Cl_2$ and the combined organic phase was washed with brine, saturated sodium bicarbonate and dried ($Na_2SO_4$), concentrated. The resulting residue was passed through a small pad of silica gel to give 7 as a colorless oil (1 g, 97%), $[\alpha]^{20}_D$=+36.5° (c 0.12 $CHCl_3$), IR ($CH_2Cl_2$) $v_{max}$ 2975.85, 1743.63, 1132.00 cm$^{-1}$. $^1$H NMR (500 MHz, $CDCl_3$) δ 5.72, (1H, t, J=4.8 Hz), 5.57 (1H, d, J=4.5 Hz), 5.23 (1H, d, J=5.0 Hz), 4.12 (1H, d, J=14.0 Hz), 4.01 (1H, d, J=13.5 Hz), 3.72 (3H, s), 1.25 (9H, s), 1.21 (9H, s), 1.18 (9H, s); $^{13}$C NMR (125.5 MHz, $CDCl_3$) δ 194.5, 177.1, 176.9, 176.8, 167.1, 72.9, 70.2, 69.4, 52.7, 38.9, 38.8, 38.7, 31.6, 27.0, 26.9 ppm; HRFABMS (M+H⁺) Calcd. 523.1543, found 523.1530.

Lactam (9a) and (9b) A solution of 7 (7 g, 13.4 mmol) and 2-aminoethanethiol (1.24 g, 16.1 mmol) in methanol (250 mL) was stirred at room temperature for one hour, followed by addition of sodium cyanoboron hydride (1.26 g, 20 mmol). The reaction mixture was stirred overnight and sodium carbonate was added to facilitate the lactam cyclization. After stirred for several hours, the suspension was filtered and concentrated. The residue was purified by column chromatography (10:1 Hexanes/Acetone) to yield two lactam diastereomers 9a and 9b (total 4.64 g, 73.6%), the ratio is 2.5:1.

Lactam 9a (3.31 g, 52.6%) was given as a white solid, m.p. 188-190° C., $[\alpha]^{20}_D$=+12.6° (c 0.1 CHCl$_3$), IR (CHCl$_3$) $v_{max}$ 1744.54, 1685.34 cm$^{-1}$. $^1$H NMR (500 MHz, CDCl$_3$) δ 5.53 (1H, t, J=10.5 Hz), 5.30 (1H, d, J=11.0 Hz), 5.19 (1H, dd, J=10.5, 8 Hz), 4.94 (1H, dt, J=13.5, 3 Hz), 3.53 (1H, ddd, J=9.8, 8.4, 3.4 Hz), 2.87 (1H, td, J=14.3, 2.5 Hz), 2.66 (1H, td, J=13.0, 3.0 Hz), 2.61-2.49 (3H, m); 1.21 (9H, s), 1.17 (9H, s), 1.12 (9H, s); $^{13}$C NMR (125.5 MHz, CDCl$_3$) δ 177.4, 177.1, 176.6, 164.3, 70.4, 69.4, 67.8, 60.2, 44.7, 38.9, 38.7, 31.8, 27.1, 26.6 ppm. HRFABMA (M+H$^+$) calcd. 472.2369, found 472.2379.

Lactam 9b (1.33 g, 21.0%) was given as a white solid, m.p. 179-181° C. IR (CH$_2$Cl$_2$) $v_{max}$ 1741.07, 1679.15, 1137.70 cm$^{-1}$; $^1$H NMR (500 MHz, CDCl$_3$) δ 5.76 (1H, t, J=10.3 Hz), 5.27 (1H, dd, J=11.5, 6.3 Hz), 4.78 (1H, m), 4.02 (1H, ddd, J=11.8, 6.3, 2.0 Hz), 3.07 (1H, t, 12.3 Hz), 2.98-2.88 (3H, m), 2.50 (1H, d, J=13.0 Hz), 2.35 (1H, m), 1.20 (9H, s), 1.17 (9H, s), 1.14 (9H, s); $^{13}$C NMR (125.5 MHz, CDCl$_3$) δ 177.42, 176.82, 163.67, 67.66, 67.03, 59.23, 47.05, 38.90, 38.69, 27.74, 27.11, 27.06, 26.96, 26.34 ppm. FABMS (M+H$^+$) calcd. 472.2369, found 472.2371.

Figure 2:
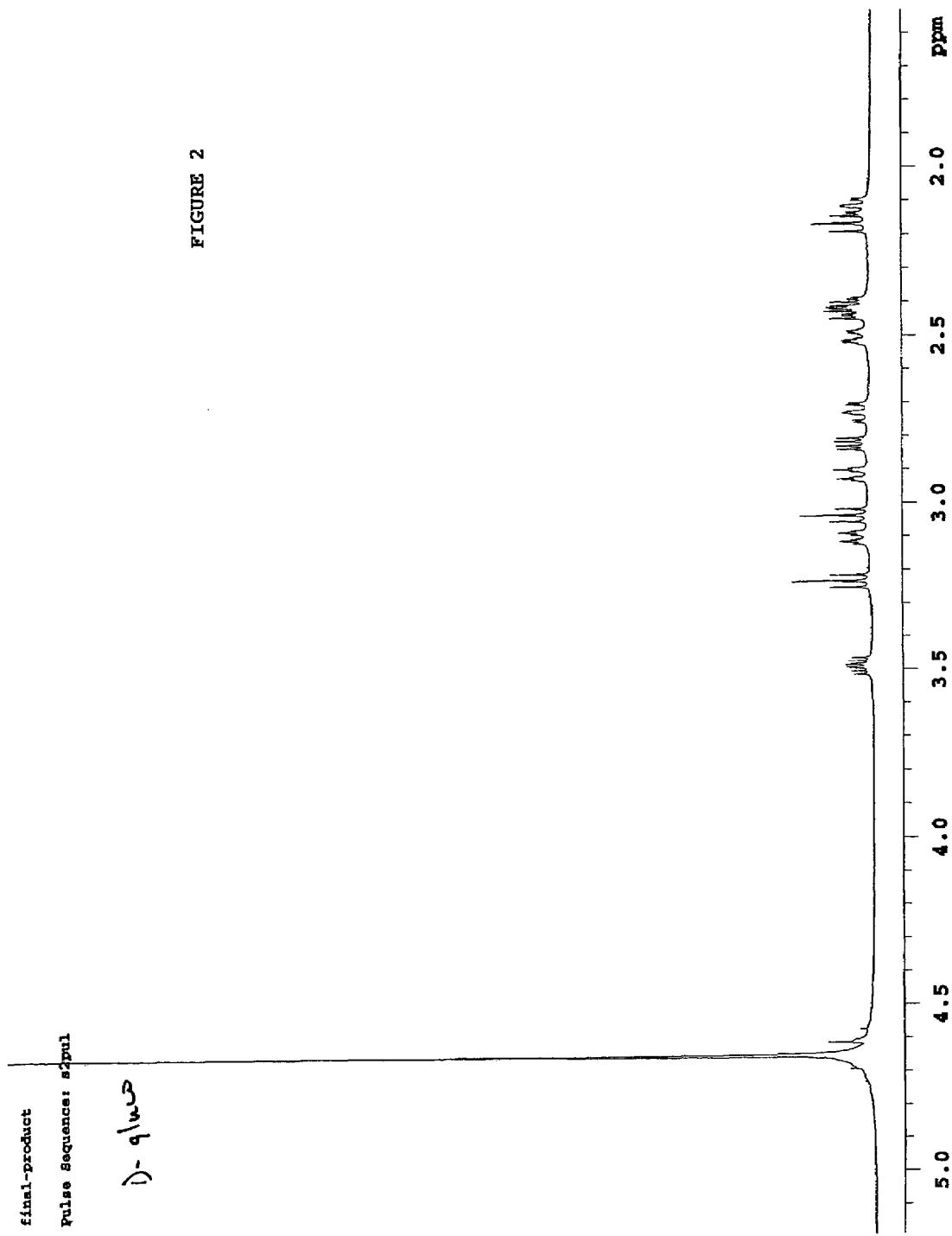
FIG. 2 is the $^1$H-NMR spectrum for the D-gluco compound 3.
Figure 3:
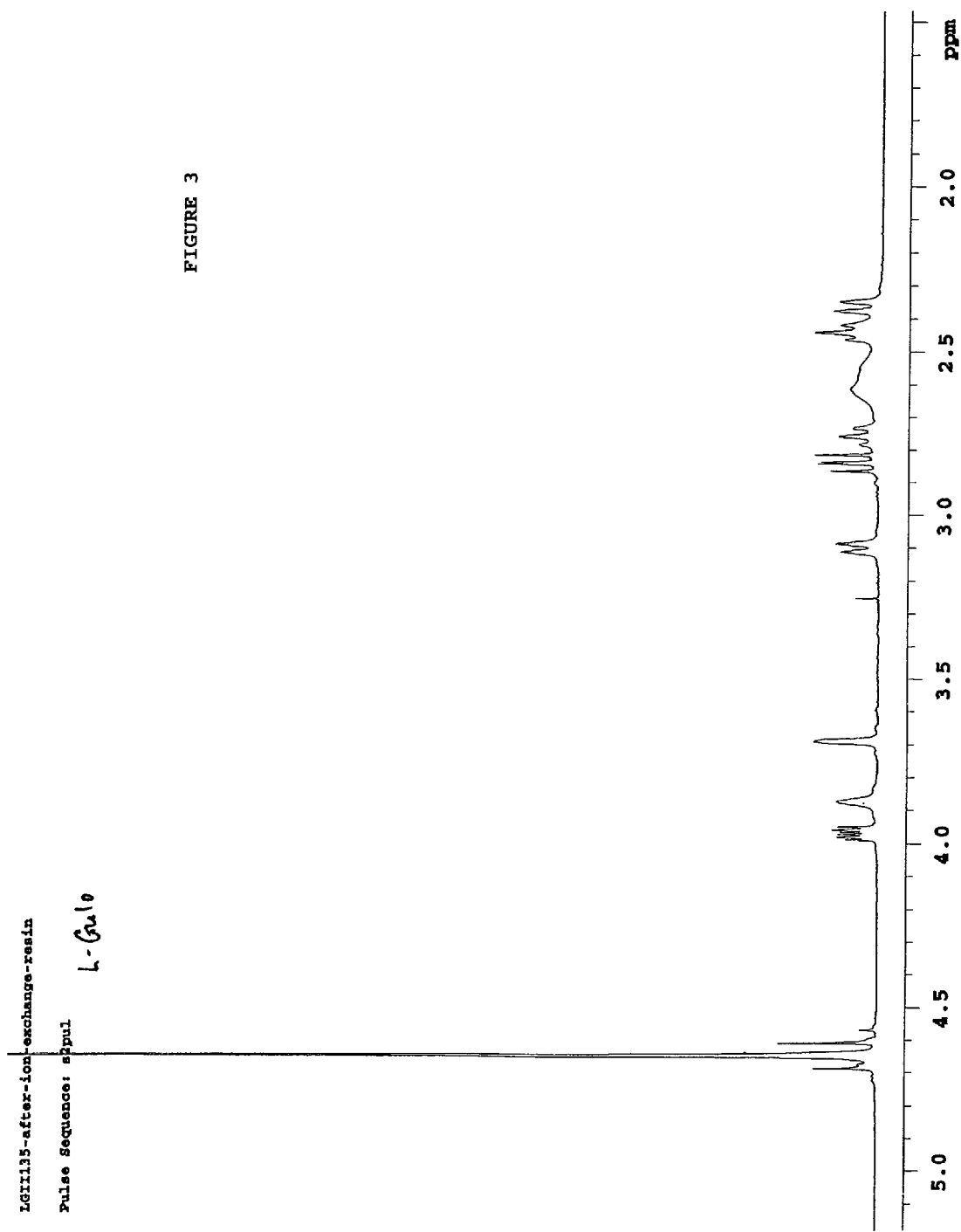
FIGS. 3, 4 and 5 show the $^1$H-NMR spectra for the L-gulo, D-ido and D-manno compounds respectively.
Figure 4:
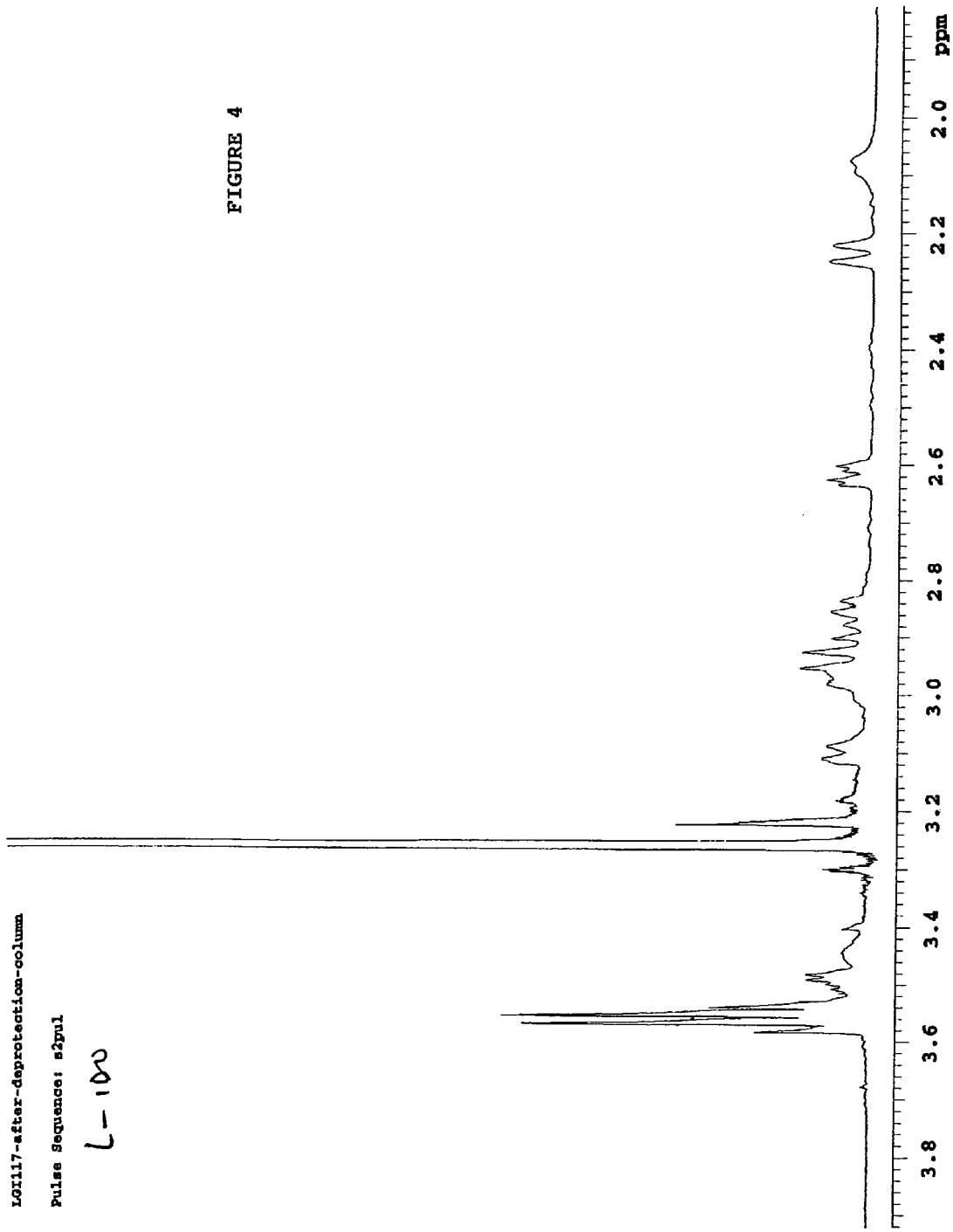
Figure 5:
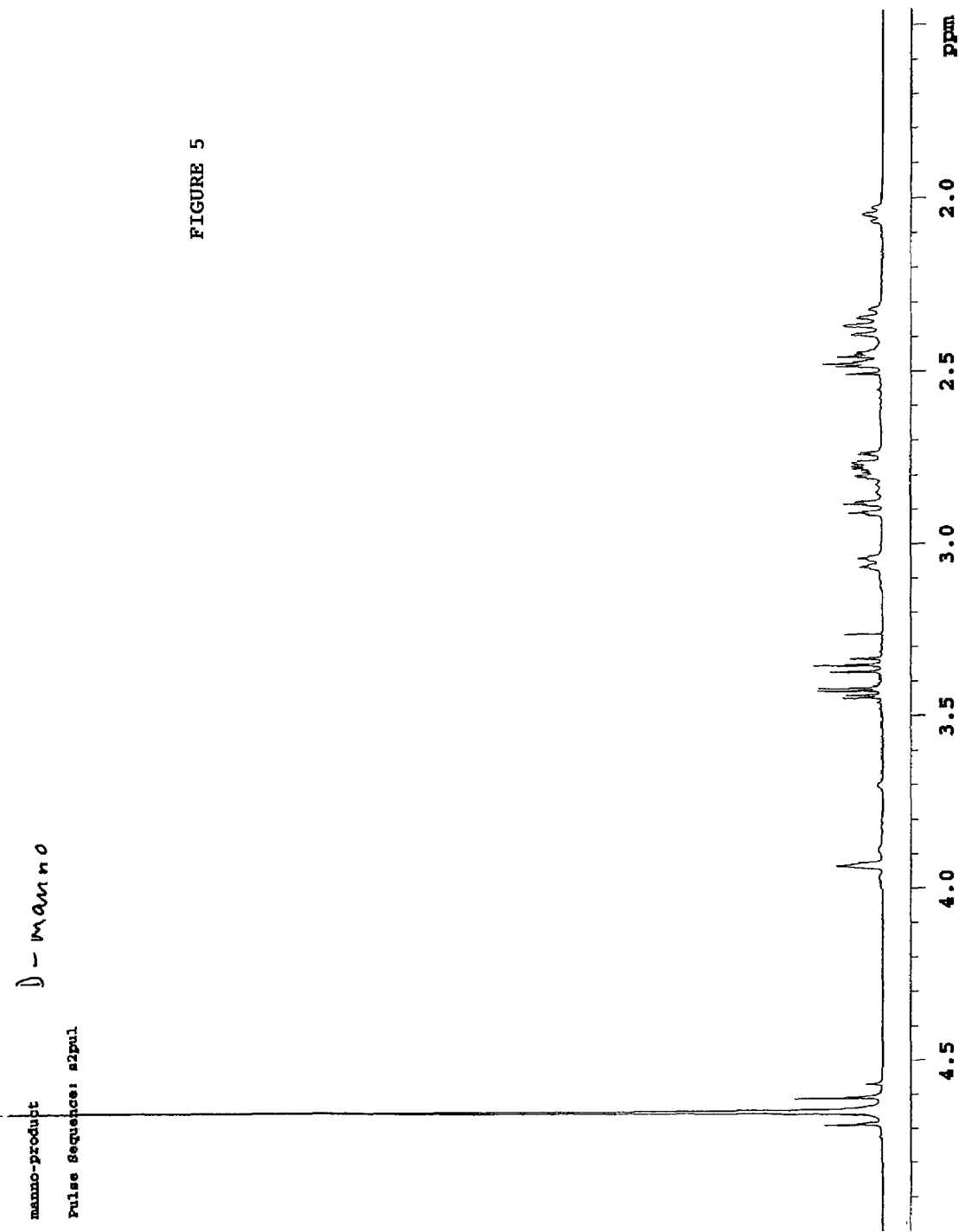

7(S),8(R),9(R),10(S)-Trihydroxy-2-thiaquinolizidine (3) A solution of lactam 9a (2 g, 4.24 mmol) and BH$_3$-THF (20 mL, 1.5M) in anhydrous THF (30 mL) was refluxed for 4 hours and the TLC and NMR showed the completion of the reduction. The solvent was removed and methanol was added and concentrated for 3 times. The residue was dissolved in methanol (30 mL), followed by addition of NaOMe (0.15 g, 2.8 mmol). The reaction was stirred for 8 hours and concentrated. The residue was applied to an ion exchange column (Dowex 50WX8-400, 30 g), which was washed with water (50 mL) and eluted with NH$_4$OH (50 mL). The elution was concentrated and purified by column chromatography (15:1 CH$_2$Cl$_2$/MeOH) to afford a white solid (0.62 g, 71%), m.p. 235-237° C.; $[\alpha]^{20}_D$=+20.2° (c 0.06H$_2$O); IR (KBr) $v_{max}$ 3355.78, 3275.61 cm$^{-1}$; $^1$H NMR (500 MHz, CDCl$_3$) δ 3.50 (1H, ddd, 11.0, 9.1, 4.9 Hz), 3.25 (1H, t, J=9.3 Hz), 3.12 (1H, dt, J=12.5, 3.0 Hz), 3.06 (1H, t, J=9.5 Hz), 2.93 (1H, dt, J=14.0, 2.5 Hz), 2.84 (1H, dd, J=11.5, 5.0 Hz), 2.75 (1H, td, J=13.0, 3.0 Hz), 2.52 (1H, m), 2.45 (1H, t, J=12.3 Hz), 2.43 (1H, m), 2.19 (1H, t, J=11.3 Hz), 2.13 (1H, td, J=10.0, 2.5 Hz); $^{13}$C NMR (125.5 MHz, CDCl$_3$) δ 77.9, 74.1, 68.5, 65.6, 59.4, 55.7, 29.3, 26.3 ppm. HR-FABMS (M+H$^+$) calcd. 206.0851, found 206.0849. The $^1$H NMR spectra is shown in FIG. 2. The analogous glycoside lactams and the 2-thiaquinolizidines are prepared in the same manner as shown in Scheme 1 and Example 1. The NMR spectra for the L-gulo, D-ido and D-manno are shown in FIGS. 3, 4 and 5.

Inhibition Assays:

The inhibitory activity of 3 against a series of enzyme was tested. Enzymes were assayed according to standard procedures (Halvorson, H. O., *Methods Enzymol.* 8, 55 (1966)) by following the hydrolysis of nitrophenyl glycosides spectrophotometrically or by evaluating the reducing sugar formed in some glucosidase assays. The enzymes used were α-glucosidase (yeast and rice), β-glucosidase (almond), α-galactosidase (green coffee beans), β-galactosidase (*E. coli*) and α-mannosidase (jack beans).

Inhibitory potency of 3 was determined by spectrophotometrically measuring the residual hydrolytic activities of the glycosidases against the corresponding nitrophenyl α- or β-D-glucopyranoside. The glycosidases used were α-glucosidase (yeast), α-glucosidase (rice), β-glucosidase (almond), α-galactosidase (green coffee beans), β-galactosidase (*E. coli*) and α-mannosidase (jack beans). All enzymes were purchased from Sigma. Each assay was performed in a phosphate or an acetate buffer at the optimal pH for each enzyme. Inhibition studies (except rice α-glucosidase) were performed by adding the inhibitor to a final concentration of 0.05 mM to 11 mM to the respective buffer solutions along with enzyme. The solutions were incubated at 37° C. before adding substrates to the solutions. The absorbance of the resulting mixture was determined at 400 nm (for p-nitrophenol).

7(S),8(R),9(R),10(S)-Trihydroxy-2-thiaquinolizidine 3 displayed competitive inhibition against both yeast and rice α-glucosidase (FIGS. 6A and 6B) with $K_i$ of 330 μM and 900 μM for yeast enzyme and rice enzyme, respectively. No inhibitory activity towards β-glucosidase (almond), α-galactosidase (green coffee beans), β-galactosidase (*E-coli*) and α-mannosidase (jack bean) was observed.

Figure 6A:
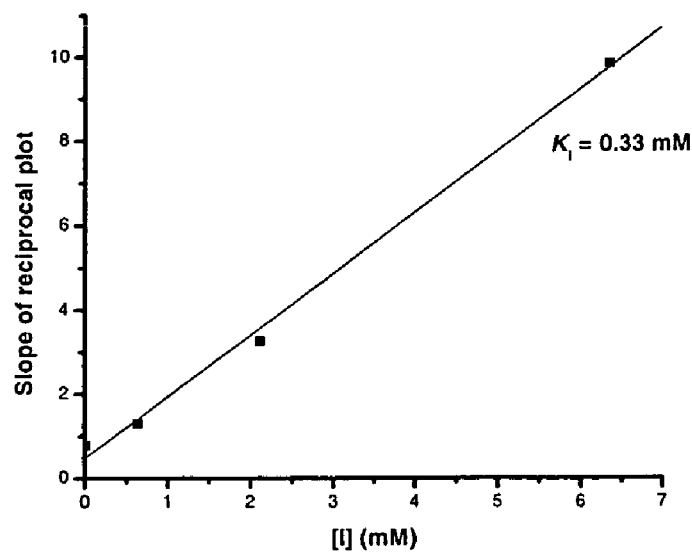
FIGS. 6A and 6B are graphs showing $K_i$ for yeast and rice α-glucosidase inhibited by compound 3, respectively.

FIG. 6A shows a slope obtained from the double reciprocal plots of initial rates and substrate concentrations (1/$v_o$ vs 1/substrate concentration) plotted against inhibitor concentration for 7(S),8(R),9(R),10(S)-trihydroxy-2-thiaquinolizidine (3) using yeast α-glucosidase and p-nitrophenylglucoside as substrate.

Figure 6B:
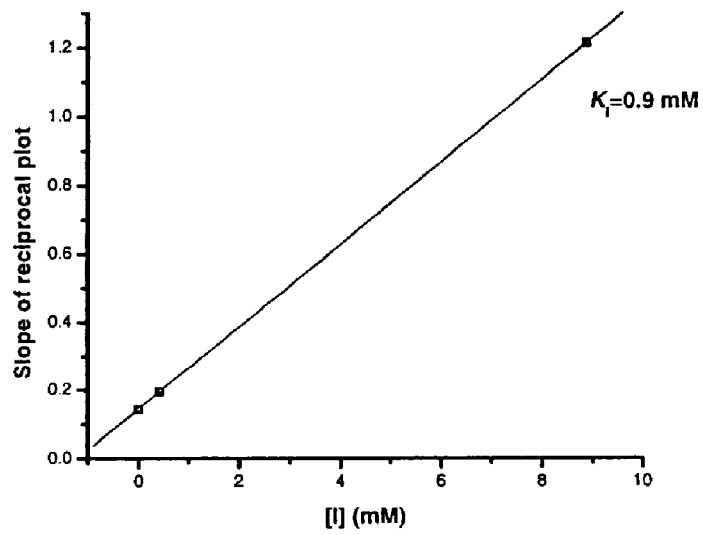

FIG. 6B shows a similar plot for (3) where the enzyme is rice α-glucosidase and the rate is monitored by a coupled enzyme reaction in which freed glucose from maltose is oxidized to gluconic acid by glucose oxidase.

X-ray analysis (FIG. 7) indicated a trans-diequatorial type fusion between the rings giving the molecule an overall flat geometry. The expected intermediate oxocarbenium species (FIG. 8) is very flat because of the double bond character between the ring oxygen and C-1.

Figure 7:
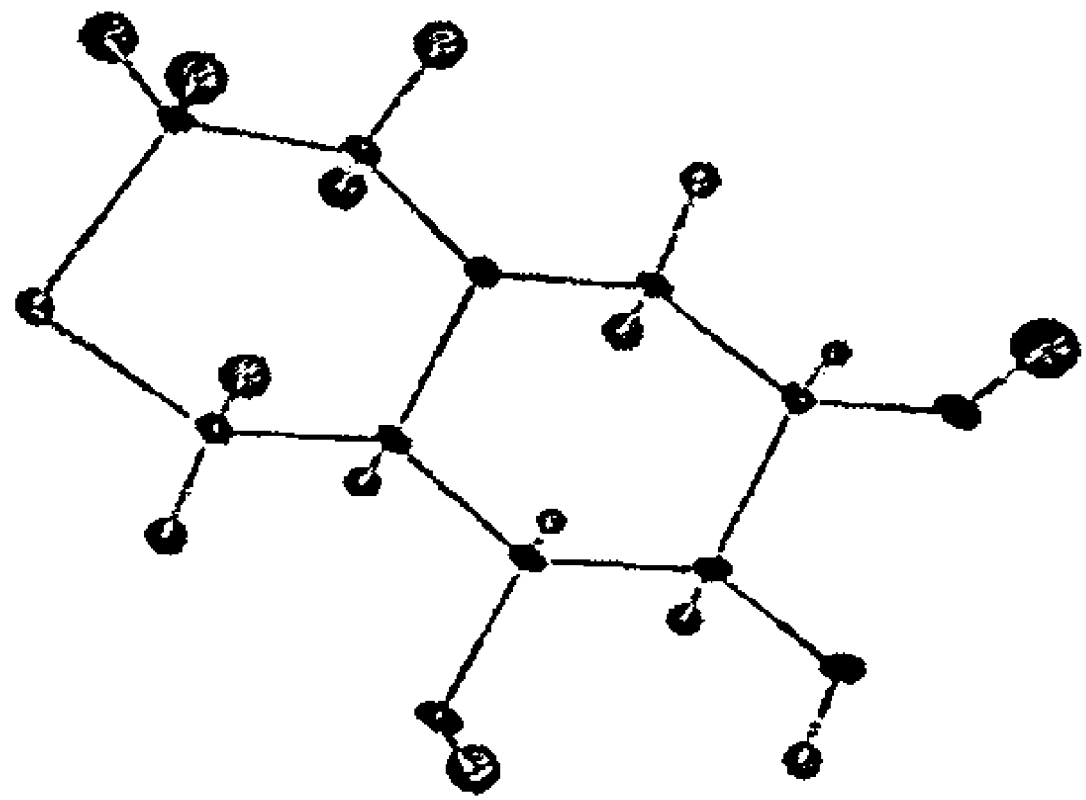
FIG. 7 is a three dimensional x-ray drawing showing an ellipsoid plot of x-ray structure of 7(S),8(R),9(R),10(S)-trihydroxy-2-thiaquinolizidine showing the trans-type ring junction and overall flat geometry.

FIG. 7 shows an ellipsoid plot of X-ray structure of 7(S),8(R),9(R),10(S)-trihydroxy-2-thiaquinolizidine showing the trans-type ring junction and overall flat geometry.

Figure 8:
FIG. 8 is a drawing showing a structure of oxycarbenium intermediate in the hydrolysis of glucosides from an ab initio calculation showing equipotential contours. The positive charge on the ring nitrogen of the oxycarbenium ion is mimicked by the protonated nitrogen in the thiaquinolizidine and other aza-sugars.

FIG. 8 shows a structure of oxycarbenium intermediate in the hydrolysis of glucosides from an ab initio calculation showing equipotential contours. The new inhibitor was active only against α-glucosidases. No inhibition of β-glucosidases was observed. This is consistent with the observation that deoxynojirimycin type inhibitors with nitrogen atom at the ring oxygen position are more selective for α-glucosidase (Wong, C.-H., et al., *Angew. Chem., Int. Ed. Engl.,* 34 521 (1995); Gijsen, H. J. M., et al., *Chem. Rev.* 96 443 (1996); Ganem, B. B. *Acc. Chem. Res.,* 29 340 (1996)). Assuming that these inhibitors are protonated in the active site of the enzyme, these results suggest that an oxocarbenium ion with positive charge at ring oxygen is an important transition state for α-glucosidases.

One of the major problems with the use of iminosugars and their derivatives as inhibitors is the lack of specificity. The activities and specificities of the known aza-bicyclic systems and key monocyclic systems are shown in Table 1.

TABLE 1

Comparison of Inhibition Activity $K_i$, μM ($IC_{50}$, μM) for iminoalditol transition state analogs

| Enzymes | 3 | 1[1] | 10[2] | 11[3] | 2[1] | 12[4,5] |
|---|---|---|---|---|---|---|
| α-glucosidase (yeast) | 330 | >1500 | n.d.[a] | $IC_{50}$ > 2000 | 12.6 | ~10 |
| α-glucosidase (rice) | 900 | 0.015 | n.d. | n.d. | 0.01 | n.d. |
| β-glucosidase (almond) | n.i.[b] | 1.5 | n.i. | $IC_{50}$ > 2000 | 47 | 8 |
| α-galactosidase (green coffee beans) | n.i. | n.d. | n.i. | n.d. | n.d. | ~10 |
| β-galactosidase (E. Coli) | n.i. | n.d. | n.d. | n.d. | n.d. | ~10 |
| α-mannosidase (jack beans) | n.i. | n.d. | n.d. | $IC_{50}$ > 2000 | n.d. | 9 |

[a]Not determined
[b]No inhibition observed
1-Legler, G., Adv. Carbohydr. Chem. Biochem. 48 319-384 (1990);
2-Van Hooft, P.A. V., et al., Org. Lett. 3,731 (2001);
3-Pearson, W.H., et al., J. Org. Chem. 61 5537 (1996);
4-Tong, M.K., et al., J. Am. Chem. Soc. 112, 6137 (1990);
5-Ganem, B., et al., J. Am. Chem. Soc. 113, 8984 (1991).

One important conclusion that can be made from Table 1 is that good inhibitory activity comes at the expense of specificity. There is no example where this is not the case. The last two entries are very effective inhibitors (low $K_i$ values) but show poor specificity. Castanospermine (an octahydro-indolizine) was the most active bicyclic system. It showed poor activity against yeast α-glucosidase but strongly inhibited the rice enzyme. However, it showed non-selectivity by inhibiting almond β-glucosidase. 7(S),8(R),9(R),10(S)-Trihydroxy-2-thiaquinolizidine (3) was superior ($K_i$ of 330 μM) against and selective for yeast α-glucosidase compared to castanospermine. It also inhibited rice α-glucosidase although the $K_i$ was relatively high. No inhibitory activity towards β-glucosidase (almond), α-galactosidase (green coffee beans), β-galactosidase (E-coli) and α-mannosidase (jack bean) was observed. A bicyclic non-aza system 13 with similar $K_i$ to 3 against yeast α-glucosidase and inactive against a β-glucosidase has been reported but no information on its specificity for the gluco-configuration was given (Arcelli, A., et al., Tetrahedron Assym. 13 191 (2002)). The octahydro-quinolizine systems such as 10 and 11 generally show very poor activity. Even the slightly ring-expanded version (Pearson, W. H., et al., J. Org. Chem. 61 5537 (1996)) (11) of the potent α-mannosidase inhibitor swainsonine (14) showed extremely poor inhibition of α-mannosidase (Table 1).

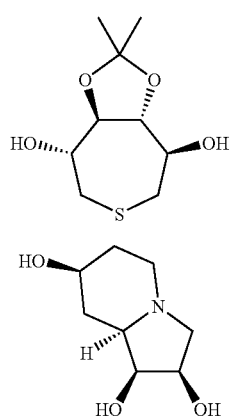

13

14

7(S), 8(R),9(R),10(S)-Trihydroxy-2-thiaquinolizidine (3) is one bicyclic system where reasonable inhibitory activity and absolute specificity for one anomer (α-) and for one configuration (D-gluco-) of sugars was obtained. This compound and castanospermine (2) are the most impressive of the known bicyclic iminosugar inhibitors with a nitrogen atom at the ring junction. Thiaquinolizidines are relatively easily accessible. Compound 3 has a much lower $K_i$ against yeast α-glucosidases than the one reported for castanospermine. In general the quinolizidines have very little or no inhibitory activity. Their ease of preparation and specificity should facilitate the development of new inhibitors and help spur advancement in this area.

For rice α-glucosidase inhibition, maltose was used as the substrate, and the assay was based on the glucose oxidase/peroxidase enzyme procedure. In this assay, the glucose released from maltose can be oxidized by glucose oxidase to generate D-gluconic acid and hydrogen peroxide. Under the catalysis of peroxidase, hydrogen peroxide reacts with dianisidine to give the oxidized form which forms a brown color. The absorbance of the solution was determined at 500 nm for oxidized o-dianisidine. The assay was performed in sodium acetate buffer at pH 4.0 at 37° C. The inhibitor was added to a final concentration of 0.4 mM and 8.9 mM to the substrate solution. The enzyme was added to the solution at 37° C., and the reaction was stopped after 10 and 30 mins by adding dilute perchloric acid solution. The glucose oxidase/peroxidase solution was pipetted into the reaction mixture, and incubate at 37° C. for 30 mins. The absorbance of the solution was determined at 500 nm.

The synthetic strategy for the preparation of compound 3 and related compounds proved to be quite efficient and direct. The relative ease of preparation of these analogs and the generality of the method opens the possibility for the preparation of a clinically relevant series of selective inhibitory compounds.

It is intended that the foregoing description be only illustrative of the present invention and that the present invention be limited only by the hereinafter appended claims.

We claim:

1. A process for the preparation of a compound (I) of the formula:

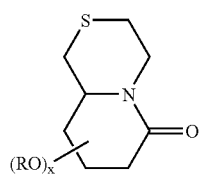

(I)

which comprises reacting a hydroxyl protected 6-bromo-5-ulosonic acid alkyl ester first with a 2-aminoalkanethiol and then with a reducing agent to produce the compound (I), wherein R is a protecting group for the reaction and x is 3.

2. The process of claim 1 wherein in addition the compound of the formula:

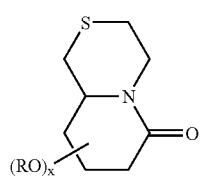

(I)

is reduced and deprotected to produce a compound (II) of the formula:

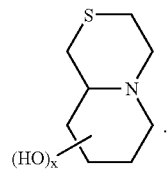

(II)

3. A process for the preparation of a compound (III) of the formula:

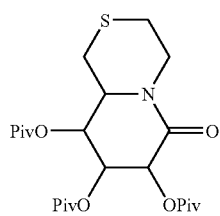

(III)

which comprises reacting 1-methyl-6-bromo-2,3,4-pivaloyl (Piv) 5-ulosonic acid ester with mercaptoethylamine and a reducing agent to produce the compound (III).

4. The process of claim 3 wherein in addition the compound (III) is reduced and deprotected to produce a compound (IV) of the formula

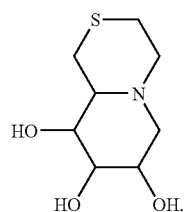

(IV)

5. The process of claim 3 wherein the compound (III) is

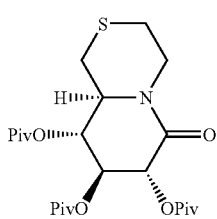 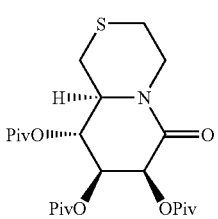

-continued

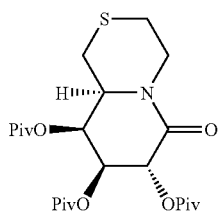 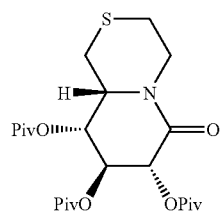 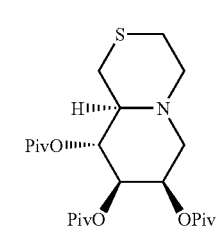

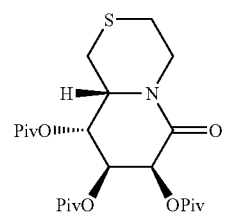 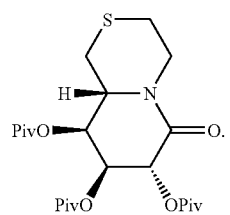

6. The process of claim 4 wherein the compound (IV) is

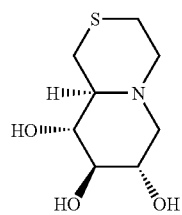 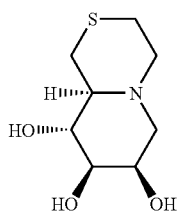

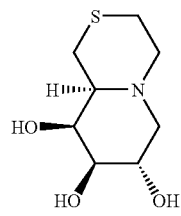 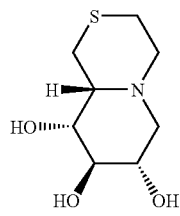

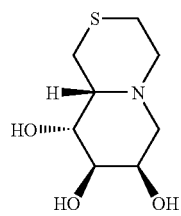 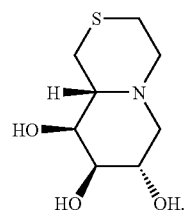

7. A compound (II) of the formula

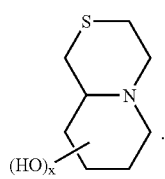

where x is 3.

8. A compound of the formula IV

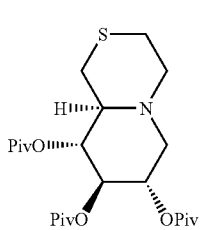 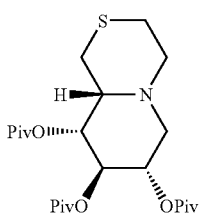

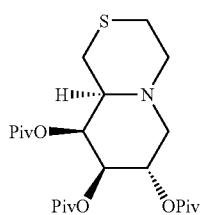 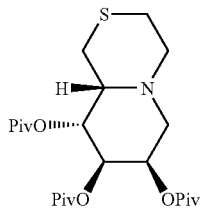 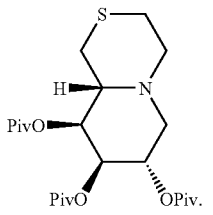

9. A compound (I) of the formula

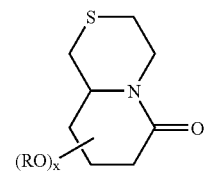

where x is 3, and R is a leaving group.

10. A method for inhibiting alpha-glycosidase which comprises reacting the enzyme with a compound (II) of the formula:

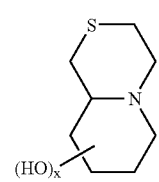

where x is 3.

11. The method of claim 10 wherein alpha-glycosidase is inhibited in vitro.

12. The method of claim 10 wherein alpha-glycosidase is inhibited in vivo in an animal.

13. A process for the preparation of a compound (II) of the formula:

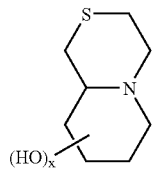

(II)

which comprises reacting a compound (I) of the formula

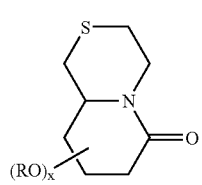

(I)

where R is a protecting group and x is 3 with a reducing agent and then a deprotecting agent to produce the compound (II).

14. The process of claim 13 wherein the compound (IV) prepared has the formula

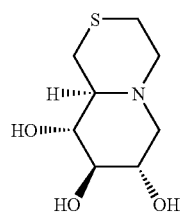

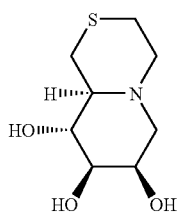

-continued

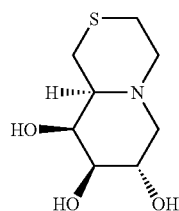

15. The process of claim 13 where R is pivaloyl and the reducing agent is borane and the deprotecting agent is sodium methoxide.

* * * * *

UNITED STATES PATENT AND TRADEMARK OFFICE
CERTIFICATE OF CORRECTION

PATENT NO.       : 7,342,010 B2                             Page 1 of 1
APPLICATION NO.  : 10/988688
DATED            : March 11, 2008
INVENTOR(S)      : Rawle I. Hollingsworth and Li Gao It is certified that error appears in the above-identified patent and that said Letters Patent is hereby corrected as shown below:

Column 9, line 35, " 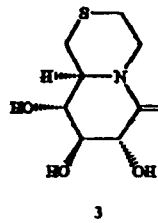 " should be -- 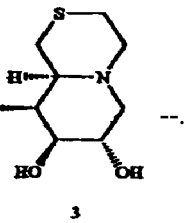 --.

Column 9, line 45, "(vii) $BH_4$" should be -- (vii) $BH_3$ --.

Signed and Sealed this

Eleventh Day of November, 2008

JON W. DUDAS
*Director of the United States Patent and Trademark Office*